US008642285B2

(12) United States Patent
Papkovsky (10) Patent No.: US 8,642,285 B2
(45) Date of Patent: Feb. 4, 2014

(54) ASSESSMENT OF CONSUMPTION OR RELEASE OF A GASEOUS ANALYTE FROM BIOLOGICAL OR CHEMICAL SAMPLES

(75) Inventor: Dmitri Boris Papkovsky, County Cork (IE)

(73) Assignee: Luxcel Biosciences Limited, Country Kildare (IE)

( * ) Notice: Subject to any disclaimer, the term of this patent is extended or adjusted under 35 U.S.C. 154(b) by 1429 days.

(21) Appl. No.: 11/918,319

(22) PCT Filed: Apr. 10, 2006

(86) PCT No.: PCT/IE2006/000028
§ 371 (c)(1),
(2), (4) Date: Oct. 12, 2007

(87) PCT Pub. No.: WO2009/109282
PCT Pub. Date: Oct. 19, 2006

(65) Prior Publication Data
US 2009/0029402 A1    Jan. 29, 2009

(30) Foreign Application Priority Data
Apr. 15, 2005  (IE) ................................. 2005/0224

(51) Int. Cl.
*C12Q 1/02*    (2006.01)
(52) U.S. Cl.
USPC .............................................. 435/29; 435/4
(58) Field of Classification Search
None
See application file for complete search history.

(56) References Cited

U.S. PATENT DOCUMENTS

| 5,232,839 A | 8/1993 | Eden et al. ...................... 435/39 |
| 5,371,016 A | 12/1994 | Berndt .......................... 435/291 |
| 5,882,922 A | 3/1999 | Tyndorf et al. ............ 435/305.3 |
| 6,080,574 A | 6/2000 | Berndt ........................ 435/288.7 |
| 2005/0064582 A1 | 3/2005 | Wittwer et al. ............ 435/287.2 |

FOREIGN PATENT DOCUMENTS

| WO | 98/15645 | 4/1998 |
| WO | 03/059518 | 7/2003 |
| WO | 2004/079349 | 9/2004 |

OTHER PUBLICATIONS

Sweet I.R. et al. Continuous Measurement of Oxygen Consumption by Pancreatic Islets, Diabetes Technology & Therapeutics, 2002, vol. 4, No. 5, pp. 661-673.*
Papkovsky D.B. Methods in Optical Oxygen Sensing: Protocols and Critical Analyses, Methods in Enzymology, 2004, vol. 381, pp. 715-735 (published online Apr. 9, 2004).*

* cited by examiner

*Primary Examiner* — Jon P Weber
*Assistant Examiner* — Satyendra Singh
(74) *Attorney, Agent, or Firm* — Jacobson Holman PLLC (57) ABSTRACT

A method for monitoring consumption or release of a gaseous analyte such as oxygen by a liquid sample under investigation includes providing a cuvette (1) having an elongate narrow tube (12) of a material which is substantially gas impermeable and which is at least partly transparent to measurement excitation radiation and emission radiation along some of the length of the tube. The tube (12) has a cross-sectional area of under 1 mm². The sample (15) is loaded into the cuvette (1), the sample being in contact with a probe in the tube (12), the probe being sensitive to the gaseous analyte, and the liquid having at least one surface and an associated headspace (16). The cuvette, the sample, and the probe are equilibrated at a target measurement temperature. Excitation radiation is directed at a sampling zone of the tube (12) and which is distal from the headspace (16), while maintaining the cuvette at the measurement temperature. The emitted radiation is measured and analysed to determine consumption or release by the sample of the gaseous analyte.

34 Claims, 4 Drawing Sheets

ASSESSMENT OF CONSUMPTION OR RELEASE OF A GASEOUS ANALYTE FROM BIOLOGICAL OR CHEMICAL SAMPLES

This is a national stage of PCT/IE06/000028 filed Apr. 10, 2006 and published in English.

FIELD OF THE INVENTION

The invention relates to assessment of consumption or release of gaseous analytes by liquid samples, such as consumption of O2 or release of CO2 by biological samples.

BACKGROUND

Quantification of molecular oxygen and rates of oxygen uptake by biological and chemical samples is an important analytical task. Rates of oxygen uptake (or release) can serve as a biomarker of cell/organism viability, metabolic status, and alterations caused by endogenous and exogenous stimuli, such as drug/effector action, disease, or pathological processes. Also, many oxygen-dependent enzymatic and chemical reactions can be monitored via oxygen consumption, thus allowing quantification of corresponding enzymes, their substrates, products and modulators of activity (i.e. inhibitors or activators).

Oxygen consumption in liquid biological samples can be quantified by measuring pressure change in the headspace of samples placed in closed test-vials containing built-in pressure sensors (U.S. Pat. No. 5,232,839). This method appears to lack sensitivity and accuracy for some applications and to be time-consuming due to high capacity of sample headspace for oxygen and rapid back-diffusion of ambient/headspace oxygen into the sample. It also appears to be difficult to apply this method to very small samples.

U.S. Pat. No. 5,371,016 and U.S. Pat. No. 6,080,574 describe optical systems for measurement of sample sterility and microbial growth, which operate with vials/tubes with fluorescence-based oxygen sensors built-into vials to which samples are added, sealed and monitored.

WO98/15645 describes a microbiological method whereby a biological sample containing living micro-organisms is assessed by measuring gradients of the dissolved oxygen, using a solid-state luminescence-based oxygen sensor.

U.S. Pat. No. 5,882,922, describes a system for measurement of oxygen consumption in samples using wells containing solid-state oxygen sensor coating applied to the bottom of each well or soluble oxygen probes added to each sample.

EP1465730 describes a two-piece sealable micro-chamber device for measurement of oxygen consumption by small biological samples, particularly those containing cells.

Other important gaseous metabolites include carbon dioxide (CO2), which is one of the main products of metabolism released by living organisms. Ammonia is also produced in considerable amounts by certain micro-organisms and biological processes. Similarly to oxygen sensing, a number of optical chemical probes and sensors for measuring these analytes have been described.

The invention is directed towards providing improvements in measuring low levels of consumption or release of such gaseous metabolites, such as O2, but also CO2, or ammonia, in small biological or chemical samples.

SUMMARY OF THE INVENTION

According to the invention, there is provided a method for monitoring consumption or release of a gaseous analyte by a specimen, the method comprising the steps of:

providing a cuvette comprising an elongate narrow tube which is substantially gas impermeable and which is at least partly transparent to measurement excitation radiation and emission radiation, the tube having a cross-sectional area of less than 2 mm$^2$;

loading a specimen under investigation into the cuvette, the cuvette containing a probe which is sensitive to the gaseous analyte, directing excitation radiation at a sampling zone of the tube and measuring emission radiation from the sampling zone, and analysing the emission radiation to determine consumption or release by the specimen of the gaseous analyte.

In one embodiment, the cuvette has a cross-sectional area of less than 1.0 mm$^2$.

In another embodiment, the specimen is introduced into the cuvette tube to a column length of at least 10 mm.

In a further embodiment, the column length is in the range of 20 mm to 100 mm.

In one embodiment, the column length is in the range of 20 mm to 50 mm.

In another embodiment, the specimen is contained in a liquid sample.

In a further embodiment, the method comprises the step of controlling temperature such that the cuvette and specimen are equilibrated at a target measurement temperature during monitoring.

In one embodiment, the temperature is controlled so that the target temperature is reached within 1 minute.

In another embodiment, the temperature is maintained during measurement with an accuracy of better than +/−0.5° C.

In a further embodiment, the target temperature is maintained for a target time duration, and the temperature is subsequently ramped to a different target temperature for successive measurement phases.

In one embodiment, the cuvette is open at both ends, and the specimen is loaded into the cuvette by dipping in a bath so that the specimen rises up the cuvette tube by capillary action.

In another embodiment, the cuvette is open at both ends, and the specimen is loaded into the cuvette by suction.

In a further embodiment, the sampling zone is at a median location between the surfaces of the specimen.

In one embodiment, the cuvette is maintained at a substantially vertical orientation, the lower end of the cuvette being capped with a support.

In another embodiment, the cuvette is maintained at a horizontal orientation.

In a further embodiment, the cuvette is sealed at one end.

In one embodiment, the sampling zone is adjacent the sealed end of the cuvette.

In another embodiment, a plurality of cuvettes are supported in a carousel and the carousel is rotated before or during measurement.

In a further embodiment, the probe is introduced with the specimen.

In one embodiment, the probe is dissolved in the specimen or a sample liquid containing the specimen.

In another embodiment, the probe is contained in the cuvette before loading of the specimen.

In a further embodiment, the probe coats at least part of an inner surface of the cuvette tube at the sampling zone.

In one embodiment, the probe is present in the form of particles in the cuvette.

In another embodiment, the method comprises the further step of providing a barrier in the cuvette to reduce or prevent diffusion between the specimen or a sample liquid containing the specimen and the environment.

In a further embodiment, the specimen is a liquid or in contained in a liquid sample, and the barrier comprises a liquid in contact with a surface of the specimen or the liquid sample.

In one embodiment, the barrier comprises an oil or gel.

In another embodiment, the probe is a fluorescence or phosphorescence based probe.

In a further embodiment, the probe is oxygen-sensitive.

In one embodiment, the probe is based on a platinum(II)-porphyrin dye or a fluorescent ruthenium(II)-complex.

In another embodiment, the probe comprises a soluble oxygen-sensitive photoluminescent dye or its macromolecular conjugate, or a suspension of polymeric micro-particles impregnated with an oxygen-sensitive dye.

In a further embodiment, the probe comprises a solid-state oxygen-sensitive photoluminescent coating applied to an inner surface of the cuvette tube.

In one embodiment, the specimen comprises an oxygen-dependent enzyme or enzymatic system and its substrate.

In another embodiment, enzyme activity is determined.

In a further embodiment, concentration of enzyme substrate is determined.

In one embodiment, inhibition or activation of the enzyme by a compound present in or added to the specimen is determined.

In another embodiment, the specimen comprises cells.

In a further embodiment, the specimen is treated with effector(s) and changes in cellular respiration caused by such treatment are assessed.

In one embodiment, the specimen comprises small aquatic organisms.

In another embodiment, the organisms are treated with effectors and changes in their respiration caused by such treatment are analysed.

In a further embodiment, the effector is a drug, a chemical compound, a biological compound, a natural product/extract, or an environmental sample.

In another aspect of the invention there is provided an apparatus for monitoring consumption or release of a gaseous analyte by a specimen, the apparatus comprising a cuvette comprising an elongate narrow tube which is substantially gas impermeable and which is at least partly transparent to measurement excitation radiation and emission radiation, the tube having a cross-sectional area of less than 2 $mm^2$.

In one embodiment, the apparatus further comprises means for loading a specimen under investigation into the cuvette.

In another embodiment, the apparatus further comprises means for directing excitation radiation at a sampling zone of the tube and measuring emission radiation from the sampling zone, and means for analysing the emission radiation to determine consumption or release by the specimen of a gaseous analyte.

In a further embodiment, the cuvette tube has a cross-sectional area of less than 1.0 $mm^2$, and a length of at least 10 mm.

In one embodiment, the apparatus comprises a chamber and a temperature controller for controlling temperature such that the cuvette and specimen are equilibrated at a target measurement temperature during monitoring.

In another embodiment, the temperature is controlled so that the target temperature is reached within 1 minute.

In a further embodiment, the temperature is maintained during measurement with an accuracy of better than +/−0.5° C.

In one embodiment, the target temperature is maintained for a target time duration, and the temperature is subsequently ramped to a different target temperature for successive measurement phases.

In another embodiment, the cuvette is open at both ends, the apparatus further comprises a bath such that the specimen may be loaded into the cuvette by dipping in the bath so that the specimen rises up the cuvette tube by capillary action.

In a further embodiment, the apparatus comprises a support for supporting the cuvette at a substantially vertical orientation, the lower end of the cuvette being capped.

In one embodiment, the apparatus comprises a support for supporting the cuvette at a horizontal orientation.

In another embodiment, the cuvette is sealed at one end.

In a further embodiment, the apparatus comprises a carousel for supporting a plurality of cuvettes, and a drive for rotating the carousel.

In one embodiment, a probe coats at least part of an inner surface of the cuvette tube.

In another aspect of the invention, there is provided a method for monitoring consumption or release of a gaseous analyte by a specimen, the method comprising the steps of:

providing a cuvette comprising an elongate narrow tube which is substantially gas impermeable and which is at least partly transparent to measurement excitation radiation and emission radiation, the tube having a cross-sectional area of less than 2 $mm^2$;

loading a specimen under investigation into the cuvette, the cuvette or the specimen containing a probe which is sensitive to the gaseous analyte, directing excitation radiation at a sampling zone of the tube and measuring emission radiation from the sampling zone, and analysing the emission radiation to determine consumption or release by the specimen of the gaseous analyte.

DETAILED DESCRIPTION OF THE INVENTION

Brief Description of the Drawings

The invention will be more clearly understood from the following description of some embodiments thereof given by way of example with reference to the accompanying drawings, in which.

DESCRIPTION OF THE EMBODIMENTS

Figure 1:
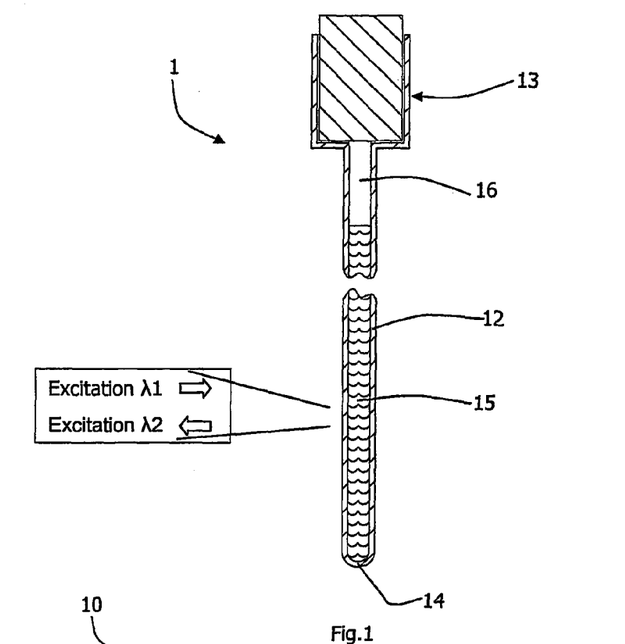
FIG. 1 is a schematic representation of a measurement cuvette sealed at one end with an oxygen consumption probe and test sample.
Figure 2:
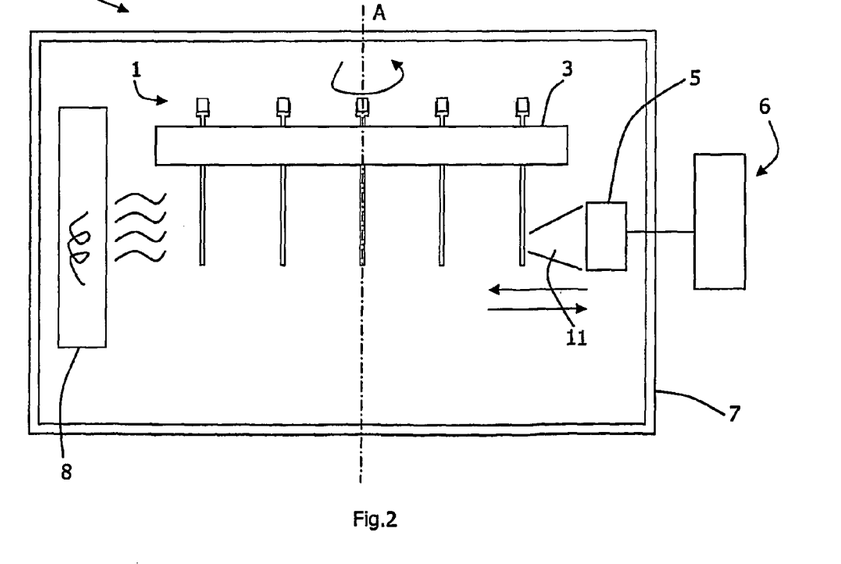
FIG. 2 is a diagrammatic elevational view illustrating an analysis system incorporating multiple cuvettes of FIG. 1.

FIG. 1 shows a cuvette 1 and FIG. 2 shows a system 10 incorporating multiple cuvettes 1 for analysis of biological sample respiration. The system 10 comprises a carousel 3 holding a ring (as viewed in plan) of cuvettes 1 rotating about a vertical axis. A fluorescence detector 5 is linked with system control hardware and interfacing units 6. FIG. 2 shows a path 11 for excitation and emission radiation. The carousel 3 and the detector 5 are located within a thermal chamber 7, within which there is an electrical heater/cooler 8 for maintenance of a target equilibrium temperature within the chamber 7 during measurement.

The cuvette 1 comprises a narrow and long tube 12 having an internal diameter of approximately 1 mm and a length of 50 mm. The tube 12 has a top neck 13 having a height of 6 mm and an internal diameter of 5 mm. There is a cap in the neck 13. The tube 12 is sealed at the bottom 14. The cuvette 1 also comprises a liquid sample 15 containing a specimen. In this specification the term "specimen" means the active species which consumes or releases the gaseous analyte. The specimen may be contained within a liquid sample or carrier.

The sample may also contain the analyte-sensitive probe incorporated into it. The probe produces a fluorescent response with both excitation and emission detection by the detector 5 at a measurement site 15, which is close to the bottom of the tube 12 and distal from a surface of the sample and a headspace 16. The detector comprises a filter for separating the excitation radiation from the emission wavelength. In this embodiment, these wavelengths are 480 nm and 650 nm.

In general, the cuvette tube has a length to allow a sample/probe column of at least 10 mm, preferably in the range of 20 mm to 100 mm, and most preferably in the range of 20 mm to 50 mm. The cuvette tube part has a cross-sectional area of at most 2 mm$^2$.

The cuvette is made of material which is gas-impermeable or has good gas-barrier properties, so it prevents diffusion of gaseous analyte across the cuvette walls to/from the sample. The preferred material for the cuvette is a fully gas-impermeable material such as glass. However, polymeric materials with good gas-barrier properties (e.g. polymethylmetacrylate, polyester, polyamide) can also be used for fabrication of the device, or its measurement/sample compartment.

The system 10 is for the detection of consumption/release of gaseous analytes such as oxygen (but alternatively carbon dioxide or ammonia for example) in liquid biological or chemical samples, such as those containing enzymes, live cells or small organisms.

Figure 3:
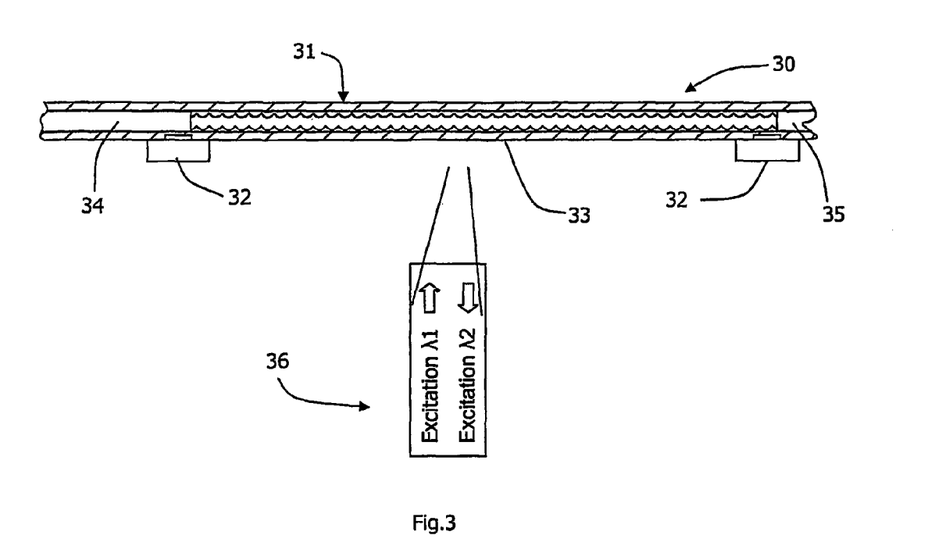
FIGS. 3 and 4 are views of alternative analysis systems of the invention, using unsealed cuvettes.

Referring to FIG. 3, a cuvette 30 has an open-ended tubular body 31 of gas-impermeable glass, supported horizontally on holders 32. A sample/probe mixture 33 is shown in the tube 31, and this diagram also shows headspaces 34 and 35.

Figure 4:
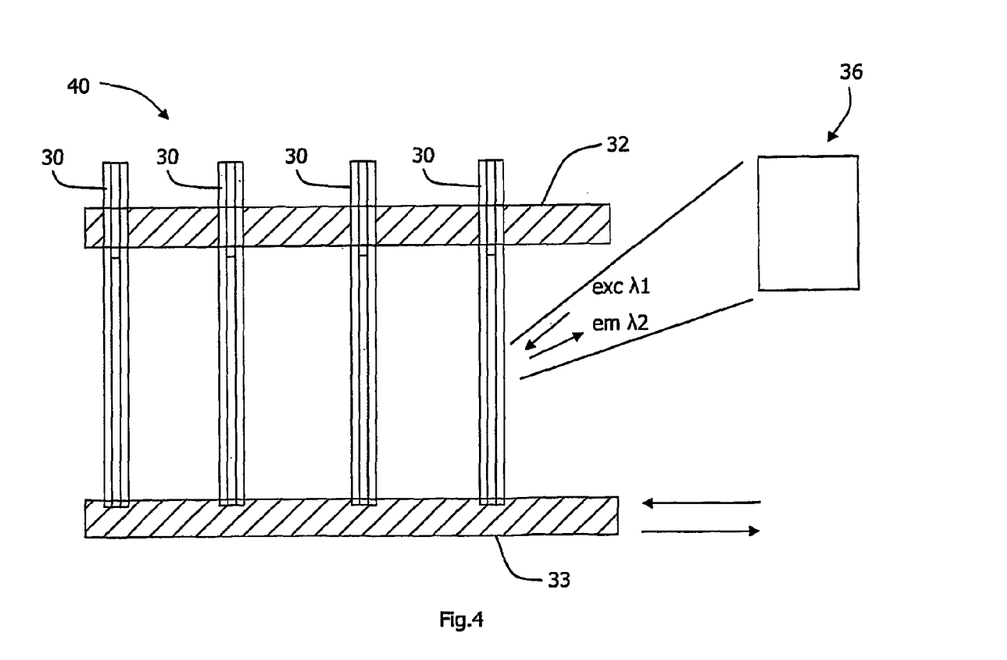

As shown in FIG. 4, there may be an assembly 40 comprising a holder 32 supporting a series of cuvettes 30, with their open lower ends in contact with a support 33. Both FIGS. 3 and 4 show a fluorescence detector 36, for measurement of fluorescence at a measurement site which is central between the ends of the sample column.

The probe is incorporated into the device or is added to the sample in such a way, that it enables measurement of the optical signal at the measurement site. This measurement site is usually the most remote part of the length of the cuvette tube from the headspace or headspaces. For the embodiments in which the cuvette is sealed at one end (for example, the cuvette 1), the measurement site is located at or close to the bottom of the cuvette. For the devices with two open ends (for example, the cuvette 30), the measurement part is located in the middle of the sample zone.

Such cuvettes provide a simple, sensitive and accurate means for monitoring consumption or release of the gaseous analyte in this part of the cuvette by quenched-fluorescence detection, which reflect the rates of consumption or release of the gaseous analyte by the sample. The cuvette configuration serves to effectively prevent the influx of ambient oxygen from the headspace (i.e. ambient air) into the sample or escape of CO2 or ammonia produced by the sample into headspace/ambient air. Therefore, it provides measurement of very small rates of analyte release/consumption by measuring local changes in analyte concentration in the sections of the sample which are relatively remote from the headspace. For measurement of consumption of gaseous analyte, the analyte begins by being dissolved in the sample and it is consumed during the measurement. An example is dissolved oxygen. For measurement of release of gaseous analyte (such as carbon dioxide) there is not necessarily any analyte to begin with, but as the measurement progresses it is released by the sample and the extent of such release is measured.

The fact that there is a large cuvette exposed surface area in relation to the sample volume allows the system to rapidly reach and maintain the desired measurement temperature. There may be one or multiple measurement temperatures, measurements being taken during each phase after equilibrating.

The probes in some embodiments are the oxygen-sensitive probes based on the phosphorescent Pt-porphyrins or fluorescent complexes of ruthenium(II), or close derivatives or analogs of these oxygen-sensitive dyes. Examples include water-soluble oxygen probes comprising hydrophilic dyes such as Pt-coproporphyrin (PtCP) or ruthenium(II)-diphenylphenantroline chloride (Ru(dpph)$_3$Cl$_2$), conjugates of these dyes with macromolecular carriers. Solid-state polymer film coatings or microparticles impregnated with hydrophobic oxygen-sensitive dyes can also be used. All these oxygen-sensitive materials display an acceptable degree of quenching by molecular oxygen at air-saturated concentrations (test samples normally have dissolved oxygen levels in this range at the start of a respirometric experiments), have convenient spectral properties and long-decay emission facilitating time-resolved fluorescence detection and/or lifetime measurements.

Among the preferred probes are soluble oxygen-sensitive probes based on the phosphorescent metalloporphyrins or ruthenium complexes. These probes, which are well known to specialists in oxygen sensing can be, for example, PtCP-BSA and Ru(dpph)3-BSA conjugates. These probes may be incorporated in the cuvette in minute quantities in solution form by mixing them with test samples which are then loaded in the cuvettes. Similarly, microparticle-based oxygen-sensitive probes can be incorporated in the cuvette or in the sample. Alternatively, solid-state oxygen-sensitive polymeric coatings (e.g. Pt-octaethylporphine or Pt-tetrakis-(pentafluorophenyl)porphine in polystyrene) can be applied to an internal surface of the cuvette tube measurement site. This enables the system to sense locally the levels of dissolved oxygen within the sample and their changes over time.

For sensing gaseous analytes such as CO2 and ammonia, fluorescent pH-sensitive probes and indicators can be used, which produce response to either acidification of sample solution caused by the release of CO2, or to alkalification caused by the release of ammonia. Fluorescent pH-indicators such as hydroxypyrenetrisulfonate, fluorescein, pH-sensitive Eu(II)-complexes in the free, conjugated or immobilised form can be used as probes. The choice of a particular pH-sensitive probe/indicator is determined by the analyte, indicator pKa, sample medium, requirements of the detector system used, and by particular application.

Because of the physical loading of the sample into the capillary cuvette, ambient oxygen from the headspace can only diffuse into the sample through very small areas at the edge(s) of the sample which is/are remote from the part of the sample where optical measurements are performed. Similarly, $CO_2$ and ammonia produced by the sample have to diffuse through a long column of liquid before they can escape into headspace.

The cuvette optical properties allow measurement of the fluorescent signal. For the systems with capillary cuvette sealed at one end, such optical measurements are carried out at the bottom part of the device, which is remote from the headspace part. In this case, diffusion of the gaseous analyte to/from these parts of the sample become rather restricted and slow, due to the long and narrow path within liquid sample acting as a barrier for diffusion. Sample mixing in the capillary tube is also greatly reduced helping to form and maintain local gradients of the gaseous analyte within the sample.

As a result, when for example oxygen gradients are developing within the sample, ambient oxygen from the headspace can not easily access the remote parts of the cuvette where optical measurements are carried out. This enables detection of very small oxygen gradients associated with low levels of oxygen consumption in the liquid sample, which otherwise are more difficult, if possible at all, to detect by prior devices developed for similar applications.

For the embodiments in which cuvettes are unsealed at both ends, optical measurements are carried out in the middle part of sample compartment which is remote from both sites of contact with headspace. For such devices, loading with test samples is achieved by simple means, such as by capillary action or by suction. After sample loading into the capillary, one or both ends of the device can be capped to avoid sample migration within the device, or the capillary can be aligned horizontally.

Sample volume is selected such that it occupies a considerable length of the tubular part of the cuvette, usually about 20-50 mm. For the particular dimensions of the cuvettes 1 and 30, 5-30 μl sample volumes are used, but these may vary, particularly for cuvettes with other dimensions. For the cuvettes sealed at one end, spinning may be applied after the addition of test samples into the loading part, to facilitate bringing the samples to the bottom of the cuvette and removing air bubbles from it.

The majority of chemical and biological processes associated with oxygen consumption (for example, enzymatic reactions, respiration and metabolic activity of live cells and organisms) are highly temperature-dependent, so as most of the oxygen-sensitive probes and materials. The same is valid for $CO_2$ and ammonia release and sensing. Therefore, strict temperature control of the cuvettes and test samples during optical measurement is important, and this is achieved by active and accurate temperature control of the measurement chamber, to a tolerance of +/_0.5° C. The capillary shape of the devices and small sample volume facilitate their rapid temperature equilibration and maintenance at a constant target temperature throughout the assay. Efficient temperature control and heat exchange within the devices provide high quality experimental data. Stable baseline signals, low optical noise, reliable and accurate detection of very small changes of the optical signal from the probe are thus achieved, which achieves the ability to detect very small oxygen gradients developing within the sample. This provides very reproducible, rapid and sensitive assays based on measurement oxygen consumption or release of $CO_2$ and ammonia.

The capillary shape of the cuvette serves to reduce passive mixing of the liquid sample by convection and/or unforced agitation (e.g. during handling or measuring multiple devices). Small contact area between the sample and headspace within the cuvette also prevents evaporation of small liquid samples during measurement. This also prevents sample spillage, thus reducing the risk of contamination. On the other hand, analyte-sensitive probes and sensors within small samples can be reliably assessed by means of fluorescence, which provides high sensitivity.

The widened neck of the cuvette 1 facilitates loading of samples into its tubular (or "capillary") part, and the cap prevents spillage of cuvette contents and sample evaporation at elevated temperatures and in prolonged experiments.

Use of the system 10 comprises the following main steps:
  preparing the cuvettes, the analyte-sensitive sensor/probes, test samples and suitable fluorescent detectors for the analysis;
  placing the probes and test samples into the cuvettes, so that the sample fills a considerable part of each cuvette including the measurement site;
  placing the loaded cuvettes in the chamber, equilibrating them at a required target temperature and measuring at constant temperature a probe fluorescent signal from the part of sample compartment within the cuvette which is remote from the headspace area(s),
  determining signal changes over time and assessing on this basis the rate of analyte consumption or release by test sample, or other parameters which relate to the analyte consumption or release.

The method allows, for example, assessment of oxygen consumption rates and biological activity of test samples, and their alterations in response to various exogenous and endogenous stimuli, such as treatment with drugs/effectors. Samples containing oxygen-dependent cells, enzymes or small organisms can be treated with various toxicants and analysed in such assays to determine the impact of these toxicants on organism respiration or sample oxygen consumption.

Fluorescent or phosphorescent measurements of the oxygen probe signal can be carried out using prompt (i.e. steady-state) or time-resolved intensity measurements. Microsecond time-resolved fluorescence is a preferred detection mode, as it provides reduction of optical interferences (light scattering, autofluorescence of cells, fluorescent compounds added to the sample), particularly when working with complex biological samples and compound libraries. It provides higher signal-to-noise ratio when detecting the probe/sensor signal. Alternatively, fluorescence lifetime-based oxygen sensing methodology can be applied, using either time-domain or phase-domain measurements. Fluorescence imaging can also be applied, which provides more detailed information about the distribution of oxygen within the device and its consumption rates in different parts of the sample.

Measurement of the gaseous analyte consumption or release in test samples is usually carried out in kinetic mode, with periodic measurements of the probe signal over time. Time frame and frequency of measurements are selected based on the particular type of sample and application. The kinetic mode is preferred as it provides fine time profile of oxygen levels in test sample and their changes, i.e. more information. At the same time, for well established assays performed under similar (standard) conditions, a two-point (start and end of assay) or even end-point signal readout from the device containing sample can be used.

In a single measurement experiment, single or multiple cuvettes with test samples can be used. For example, multiple cuvettes can be used to perform parallel analysis of oxygen consumption. This is facilitated by the fact that biological oxygen consumption is generally a rather slow process, whereas the initial concentration of dissolved oxygen in samples at the time when they are placed in the device is close to air-saturated levels (200-250 µM, depending on the temperature and chemical composition). As a result, a considerable time (from several minutes to several hours) is required to achieve detectable oxygen gradients in such samples. In this case, multiple devices and samples can be measured periodically in parallel and then corresponding signal profiles and oxygen gradients are reconstructed. Using such devices and measurement format, accurate quantification of absolute rates of oxygen consumption by the samples is possible, although the samples are not fully sealed and have contact with ambient air at headspace areas. At the same time, assessment of relative rates of oxygen consumption and their changes is more straightforward. In this case, measured signal changes for test samples are related to those of the control sample (e.g. treated samples versus untreated) which is also included in the assay or analysed in a separate experiment.

The system is very efficient in analysing very small samples and detecting very low rates of consumption of oxygen or release of carbon dioxide. It provides high sensitivity, and is also very simple and convenient to use.

If required, diffusion of the gaseous analyte to/from the sample being analysed within the cuvette can be further reduced by applying a layer of mineral oil on top of the aqueous sample, to create an additional barrier for back diffusion of the analyte from/to the headspace. This often results in some improvement of assay performance.

More generally, a system for monitoring oxygen uptake in biological samples includes some or all of the following:
- sets of cuvettes (disposable or reusable) for measurement of consumption or release of gaseous analytes by liquid biological or chemical samples by means of an analyte-sensitive fluorescence-based probe;
- a holder unit which accommodates a number of devices with test samples and the probe, facilitates the required manipulations during sample preparation and analysis, and also aligns them in certain positions to allow optical measurements;
- a detection unit which measures fluorescent signal from each of the device(s) placed in the holder, particularly from certain parts of the sample within the cuvettes which are remote from sample headspace areas, and which provides sequential or parallel measurement of the cuvettes during the assay;
- a temperature control unit which provides efficient heat exchange within the system, rapid temperature equilibration of the devices in the holder, and maintenance of constant temperature or a controlled varying temperature profile during measurement;
- mechanical and optical components which provide, if necessary, movement of the holder and/or changing of the optical alignment to allow measurement of different devices in the holder,
- additional hardware to control system operation as a whole, and software for external control and data analysis.

The system can be used for a variety of different applications. These applications include measurement of respiration of cells and sub-cellular components (e.g. mitochondrial fraction, organells), measurement of activity and inhibition of various oxygen-dependent enzymes and coupled enzymatic systems, quantification of enzyme substrates and metabolites, measurement of oxygen uptake by small aquatic organisms, provided they fit inside the device. Other applications include assessment via oxygen respiration of cell/organism viability, action on test cell/organism of various chemical and biological compounds as well as more complex samples such as natural extracts, mixtures of several components, environmental samples, or comparison of different samples to each other. Furthermore, efficient temperature control and heat exchange within the device during the respirometric experiments enables to determine in one experiment relative rates of oxygen uptake of the sample at several different temperatures. This can provide more detailed assessment of the chemical or biological samples. Similarly, application of the system of invention to the measurement of rates of release of $CO_2$ or ammonia by test samples (if occurring, applicable and measurable), also provides useful methods of assessment of chemical and biological samples.

Some applications are described in the examples below, which are non-limiting to the invention.

EXAMPLES

Example 1

Preparation of Devices and Setting Up the Respirometric Experiment Using Water-Soluble Phosphorescent Oxygen Probes The cuvettes 1 were used and the top of each capillary is attached to a plastic neck which serves as sample reservoir (accommodates ~50 µl of liquid) and which is also used for capping the cuvette during the measurement experiment (caps are provided with capillaries).

To perform a respirometric experiment, test samples were pipetted in 50 µl aliquots into the wells of standard microtiter plate and mixed with 5 µl of a phosphorescent oxygen probe (type A65N, Luxcel Biosciences, 50 µM stock solution in water). 20 µl of these samples were pipetted into the wide part of the cuvette The cuvettes were then placed in a carousel in a LightCycler™ chamber, spun for ~10 s at 5000 rpm on a centrifuge to bring the samples to the bottom of the cuvettes. After that the carousel was inserted into the LightCycler™ reader and fluorescent signals from capillaries with samples were read using 650 nm emission filter. Main instrument settings such as temperature (usually 37° C.), duration of experiment (over 30-120 minutes), the number of samples (1-40) and their location were set with the instrument software.

After the experiment was completed, measured profiles of probe fluorescent signal in each capillary were analysed to determine the rates of signal increase over time, which reflect the rates of oxygen consumption by the sample. These devices allowed sensitive detection of low levels of oxygen consumption by test samples.

Example 2

Preparation of Devices and Setting Up the Respirometric Experiment Using Solid-State Phosphorescent Oxygen Probes For the fabrication of devices with embedded solid-state oxygen sensors and their use, a LightCycler™ and cuvettes of Example 1 were employed. Bottom parts of the cuvettes were pre-coated with the polymeric oxygen-sensitive phosphorescent coatings. The coating 'cocktail' was prepared by dissolving 1 mg of platinum(II)-octaethylporphine dye (PtOEP) in 1 ml of 10% solution of polystyrene (M.W. 230,000) in ethylacetate. 2 µl of this cocktail were applied to the bottom of each cuvette with a Pasteur pipette, and allowing to dry. After solvent evaporation, a thin film coating was produced which displayed strong phosphorescence and sensitivity to oxygen (2-3-fold signal enhancement upon deoxygenation of air-saturated aqueous samples). These cuvettes with the phosphorescent oxygen sensors were used in respirometric experiments in a similar way as those with the soluble oxygen probe (see Example 1).

Example 3

Preparation of Devices with the Particle-Based Oxygen Probe

The LightCycler™ system with cuvettes described in the Example 1 were employed, but in this case a microparticle-based phosphorescent oxygen-sensitive probe was incorporated in each of the cuvettes. The probe comprises an aqueous suspension of 3.3 µm monodispersed particles (1.5% w/w), which were made of polystyrene cross-linked with divinylbenzene and doped with PtOEK dye. Impregnation was achieved by incubating the particles in PtOEP solution in chloroform (10 mg/ml) for 24 h and then washing them with isopropanol, several times with ethanol and finally with water. A small volume (2-3 µl) of this suspension of microparticles was dispensed to the capillary cuvettes with a Pasteur pipette and then dried. Alternatively, the cuvette with liquid probe was capped and stored until further use.

Upon the addition of sample to such a cuvette, the particles produced phosphorescent signals detectable by the LightCycler™ reader and marked signal response to oxygen depletion in the sample. Approximately 2-fold increase in phosphorescence was observed when changing from air-saturated to deoxygenated solution. The devices with microparticle based oxygen probes can be used in respirometric experiments in a similar way as those with the water-soluble oxygen probe (see Example 1).

Example 4

Preparation of a Respirometric Experiment with Devices Having Two Open Ends

Devices in the form of glass microcapillaries having internal diameter of approximately 0.5 mm, and length of 130 mm were produced. Such capillary cuvettes were then loaded with test sample, which also contained 5 uM of A65N oxygen-sensitive probe. This was achieved by dipping the capillary into sample solution and when the sample fills approximately 50-70 mm of capillary length (assisted with suction micropipette, if required, sample volume inside is about 10 ul), the capillary was taken out and aligned in a special holder which similar to the one shown in FIG. 1c. This holder holds the capillary in a vertical position, and also caps the bottom end of it preventing leakage of the sample. The holder with the capillary device was then aligned in sample compartment of a spectrofluorimeter Cary Eclipse™. Fluorescence from the cuvette was monitored using excitation at 535 nm and emission at 650 nm such, that excitation beam focused in horizontal plane and was incident on the cuvette at a height of approximately 20-30 mm from the bottom, i.e. in the middle of sample zone. Measured changes in probe fluorescence were correlated with the rate of oxygen consumption by the sample.

Example 5

Preparation of a Respirometric Experiment with Devices Having Two Open Ends

An experiment was carried out similar to the Example 4, but in this case cuvettes with internal diameters of approximately 0.25 mm were used (required sample volume 5-10 ul). After filling the cuvette with test sample containing the oxygen probe (approximately 50-100 mm of length), the cuvette was fixed in a special holder horizontally, without capping its ends. Fluorescence was then measured from the middle part of sample zone (~30 mm away from the loading end), using LS-50B spectrofluorometer, which has excitation beam focused in vertical plane. Measured changes in probe fluorescence were correlated with the rate of oxygen consumption by the sample.

Example 6

Monitoring of Respiration of Small Organisms

The devices and respirometric experiments were set-up as described in Example 1, in which the samples comprised small numbers of brine shrimp *Artemia salina* (small aquatic animals, ~1 mm in size) were used as test organisms in seawater. To prepare *Artemia* for the experiment, eggs were incubated in artificial seawater for 48 h at ~25° C. under continuous illumination and used for respirometric experiments carried out in artificial seawater at 30° C.

Figure 5:
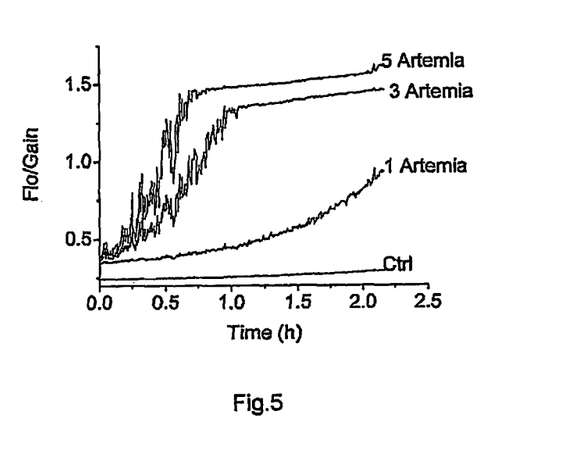
FIG. 5 shows profiles of phosphorescent signal from the capillary devices containing aqueous samples with different numbers of small aquatic organisms (*Artemia salina*), reflecting respiration activity and rates of oxygen uptake.

FIG. 5 shows that oxygen respiration of single *Artemia* in ~30 µl sample is easily detectable with the capillary system. In a separate experiment, animals were pre-treated with different compounds (chemicals and environmental toxicants) and changes in their respiration were analysed. The experiment provided detection of both reduction and enhancement of respiration of test animals with respect to untreated control animals, and determination of dose-response curve and EC50 for different effectors. Whereas using alternative respirometric formats such as 384-well plates with oil seal, or low-volume sealable microplates produced by Luxcel Biosciences, it was not possible to detect respiration of single animal (similar sample volumes were used). Sensitivity of these formats is not so good for the detection of low levels of respiration, and larger numbers of animals were required for reliable assessment.

Example 7

Measurement of Enzymatic Activity

Figure 6:
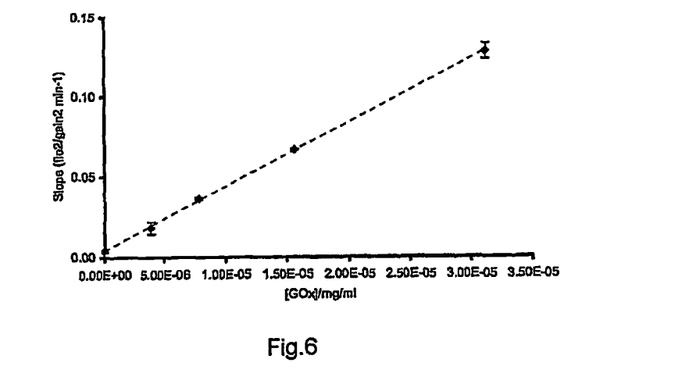
FIG. 6 shows a calibration graph showing the relationships between the rate of oxygen consumption (slope of the phosphorescent signal) and concentration of glucose oxidase enzyme in a test sample.

Respirometric system and experiment were set up as described in Example 1, but using samples comprising phosphate buffer saline, pH 7.0, containing 100 mM of glucose (substrate), to which different concentrations of glucose oxidase enzyme were added. These samples were placed in the capillaries and monitored on the LightCycler™ instrument for one hour at 25° C., to obtain slopes of the phosphorescent signal from the probe for each sample, including control sample without enzyme. Measured time profiles of phosphorescence were analysed to determine the initial slopes of the probe signal for each sample. The slopes, which reflect oxygen uptake rates by animals, were calculated as:

$$\text{Slope} = (I2 - I1)/(t2 - t1),$$

where I1 and I2—fluorescence intensities at time points t1 and t2. Resulting graph (FIG. 6) shows that this method allows monitoring of very low levels of enzyme activity (down to approximately 5 ng/ml). A similar experiment performed in standard 96-well plates on a fluorescence plate reader showed considerably lower sensitivity and greater variation of data.

In a separate experiment, samples containing fixed concentrations of glucose oxidase enzyme in phosphate buffer saline, pH 7.0 were spiked with different concentrations of glucose (ranging 0.01-100 mM) and analysed on the respirometric system with glass capillaries, to produce dose response curves. This application allows quantification of enzyme substrates such as glucose in unknown samples, using calibration produced with a set of glucose standards.

In a separate experiment, activity and inhibition of microsomal fractions of cytochrome P450 isoenzymes were measured using 100 mM K-phosphate pH 7.4, containing 3.3 mM MgCl, 1.3 mM NADP$^+$, 1.6 U/ml glucose-6-phosphate dehydrogenase, 3.3 mM Glucose-6-Phosphate as assay buffer and 5 μM of the water-soluble oxygen probe. In the presence of corresponding substrates (used at relatively high concentrations, close to their Km), it was possible to monitor with high sensitivity and reproducibility the activity of these enzymatic preparations via the consumption of dissolved oxygen. Rates of oxygen consumption measured by this assay correlated with the amount of enzyme in the sample. In a similar manner, measurement of rates of metabolism of different substrates by particular CYP450 isoenzymes (used at a constant concentration optimised in a separate experiment) was successfully achieved. Measurement of inhibition of different CYP450 isoenzymes by chemical compounds was also achieved.

Example 8

Effect of Additional Oil Seal on Assay Sensitivity

Figure 7:
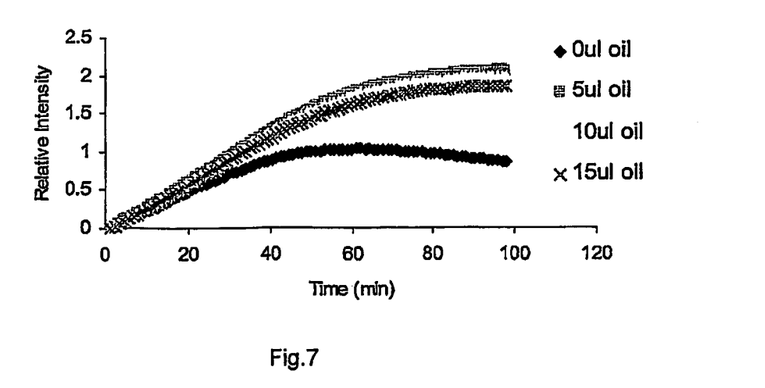
FIG. 7 shows the effect of an additional oil seal on respiration profiles of samples containing glucose oxidase enzyme and glucose, measured in the capillary cuvettes with soluble oxygen probe.

Experiments with glucose oxidase were carried out as described in Example 7, using constant enzyme concentration, 50 mM glucose concentration and 20 μl sample volume. To a number of cuvettes, 5, 10 and 15 μl aliquots of heavy mineral oil were added, so that they covered the top of the sample, while the remaining cuvettes with samples contained no oil, and then measurement of oxygen consumption was carried out on the LightCycler™ instrument at 30° C. FIG. 7 shows that for the samples with oil seal, the initial rates of oxygen consumption (initial slopes of fluorescent signal) appear to be similar to the samples without oil. On the other hand, oil seal is seen to improve assay performance, so that samples develop greater oxygen gradients (higher maximal signals) and produce respiration profiles with less pronounced hook effect. The assay is not very dependent on the amount of added oil, and samples with different volumes of oil produced practically identical results.

Example 9

Measurement of Oxygen Respiration at Different Temperatures

Experiments were carried out as described in Example 4, but using M16 growth medium and mouse embryos as test organisms. Measurements were carried out in glass cuvettes, each containing ten embryos (4-day blastocyst stage) in 20 μl of media, 5 μM of the soluble oxygen probe and mineral oil seal (10 μl). The LightCycler™ instrument was programmed to perform fluorescence measurements in samples as follows: 30 min at 30° C., then 30 min at 34° C., 30 min at 37° C. and 30 min at 40° C. Samples containing medium without embryos (air-saturated solution) and medium deoxygenated with glucose oxidase/glucose were included as controls. Measured profiles of fluorescent signals were processed to determine relative rates of oxygen consumption at different temperatures on the basis of corresponding slopes of fluorescent signals. It was determined that embryos produced maximal rates of oxygen respiration 40° C., which decreased only marginally at 37° C., but then decreased very considerably to less than 50% and less than 20% at 34° C. and 30° C., respectively.

Example 10

Measurement of the Release of CO2

An experiment was carried out as described in Example 6, using test sample which comprised a low molarity buffer, pH6, containing 100 mM of urea, 0.1 uM of fluorescein (pH-sensitive probe) and small amount of urease enzyme (added before loading). Such sample, when placed in the cuvette produced measurable increase in fluorescence of the probe, which responded to the release of ammonia in the enzymatic reaction.

The invention is not limited to the embodiments described but may be varied in construction and detail. For example, the cuvette tube may have a cross-sectional shape other than round, such as square or rectangular.

The invention claimed is:

1. A method for sensitive and accurate measurement of consumption or release of a gaseous analyte in a plurality of specimens, the method comprising the steps of:

providing for each specimen a cuvette comprising an elongate narrow tube which is sealed at one end, substantially gas impermeable and which is at least partly transparent to measurement excitation radiation and emission radiation, the tube having a cross-sectional area of less than 2 mm$^2$;

loading specimens under investigation into the cuvettes, each cuvette containing a probe which is sensitive to the gaseous analyte, placing the cuvettes with loaded specimens in a measurement holder and providing them with rapid, stable and efficient temperature control at a selected target temperature with an accuracy of at least +/−0.5° C. for the duration of measuring emission radiation of the probe;

periodically directing excitation radiation at a sampling zone located at or close to the bottom of each cuvette with loaded specimen and measuring emission radiation of the probe locally within the sampling zone, and analyzing the changes in emission radiation over time for each cuvette with loaded specimen and determining on the basis of these local changes the rate of consumption or release of the gaseous analyte by each specimen.

2. The method according to claim 1, wherein the cuvette has a cross-sectional area of less than 1.0 mm$^2$.

3. The method as claimed in claim 1, wherein the specimen is introduced into the cuvette tube to a column length of at least 10 mm.

4. The method according to claim 3, wherein the column length is in the range of 20 mm to 100 mm.

5. The method according to claim 4, wherein the column length is in the range of 20 mm to 50 mm.

6. The method according to claim 1, wherein the specimen is contained in a liquid sample.

7. The method according to claim 1, wherein the temperature is controlled so that the target temperature is reached within 1 minute.

8. The method according to claim 1, wherein the temperature is maintained during measurement with an accuracy of better than +/−0.5° C.

9. The method according to claim 1, wherein the target temperature is maintained for a target time duration, and the temperature is subsequently ramped to a different target temperature for successive measurement phases.

10. The method according to claim 1, wherein the cuvette is maintained at a substantially vertical orientation, the lower end of the cuvette being capped with a support.

11. The method according to claim 1, wherein the cuvette is maintained at a horizontal orientation.

12. The method according to claim 1, wherein the plurality of cuvettes are supported in a carousel and the carousel is rotated before or during measurement.

13. The method according to claim 1, wherein the probe is introduced with the specimen.

14. The method as claimed in claim 13, wherein the probe is dissolved in the specimen or a sample liquid containing the specimen.

15. The method according to claim 1, wherein the probe is contained in the cuvette before loading of the specimen.

16. The method according to claim 15, wherein the probe coats at least part of an inner surface of the cuvette tube at the sampling zone.

17. The method according to claim 15, wherein the probe is present in the form of particles in the cuvette.

18. The method according to claim 1, comprising the further step of providing a barrier in the cuvette to reduce or prevent diffusion between the specimen or a sample liquid containing the specimen and the environment.

19. The method according to claim 18, wherein the specimen is a liquid or is contained in a liquid sample, and the barrier comprises a liquid in contact with a surface of the specimen or the liquid sample.

20. The method according to claim 19, wherein the barrier comprises an oil or gel.

21. The method according to claim 1, wherein the probe is a fluorescence or phosphorescence based probe.

22. The method according to claim 1, wherein the probe is oxygen-sensitive.

23. The method according to claim 1, wherein the probe is based on a platinum(II)-porphyrin dye or a fluorescent ruthenium(II)-complex.

24. The method according to claim 21, wherein the probe comprises a soluble oxygen-sensitive photoluminescent dye or its macromolecular conjugate, or a suspension of polymeric micro-particles impregnated with an oxygen-sensitive dye.

25. The method according to claim 21, wherein the probe comprises a solid-state oxygen-sensitive photoluminescent coating applied to an inner surface of the cuvette tube.

26. The method according to claim 1, wherein the specimen comprises an oxygen-dependent enzyme or enzymatic system and its substrate.

27. The method according to claim 26, wherein enzyme activity is determined.

28. The method according to claim 27, wherein concentration of enzyme substrate is determined.

29. The method according to claim 27, wherein inhibition or activation of the enzyme by a compound present in or added to the specimen is determined.

30. The method according to claim 1, wherein the specimen comprises cells.

31. The method according to claim 30, wherein the specimen is treated with effector(s) and changes in cellular respiration caused by such treatment are assessed.

32. The method according to claim 1, wherein the specimen comprises small aquatic organisms.

33. The method according to claim 32, wherein the organisms are treated with effectors and changes in their respiration caused by such treatment are analysed.

34. The method according to claim 33, wherein the effector is a drug, a chemical compound, a biological compound, a natural product/extract, or an environmental sample.

* * * * *

UNITED STATES PATENT AND TRADEMARK OFFICE
CERTIFICATE OF CORRECTION

PATENT NO. : 8,642,285 B2 Page 1 of 1
APPLICATION NO. : 11/918319
DATED : February 4, 2014
INVENTOR(S) : Dmitri Boris Papkovsky It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1565 days.

Signed and Sealed this
Twenty-ninth Day of September, 2015

Michelle K. Lee
*Director of the United States Patent and Trademark Office*